United States Patent [19]

Blake, III et al.

[11] Patent Number: 4,986,813
[45] Date of Patent: Jan. 22, 1991

[54] DISPOSABLE HYPODERMIC SYRINGE

[75] Inventors: Joseph W. Blake, III, New Canaan; Thomas E. Sloane, Jr., West Reading, both of Conn.

[73] Assignee: The MadTech Group, Inc., South Plainfield, N.J.

[21] Appl. No.: 296,495

[22] Filed: Jan. 12, 1989

Related U.S. Application Data

[63] Continuation-in-part of Ser. No. 150,621, Feb. 8, 1988, abandoned.

[51] Int. Cl.⁵ .............................................. A61M 5/32
[52] U.S. Cl. .................................. 604/110; 604/195; 604/240
[58] Field of Search ............... 604/110, 263, 196, 197, 604/195, 240

[56] References Cited

U.S. PATENT DOCUMENTS

| | | | |
|---|---|---|---|
| 4,507,117 | 3/1985 | Vining et al. | 604/196 |
| 4,553,962 | 11/1985 | Brunet | 604/198 |
| 4,675,005 | 6/1987 | DeLuccia | 604/110 |
| 4,692,156 | 9/1987 | Haller | 604/195 |
| 4,710,170 | 12/1987 | Haber et al. | 604/110 |
| 4,747,830 | 5/1988 | Gloyer et al. | 604/110 |
| 4,770,655 | 9/1988 | Haber et al. | 604/110 |
| 4,790,822 | 12/1988 | Haining | 604/110 |
| 4,804,370 | 2/1989 | Haber et al. | 604/195 |
| 4,826,484 | 5/1989 | Haber et al. | 604/110 |
| 4,850,994 | 7/1989 | Zerbst et al. | 604/198 |
| 4,883,471 | 11/1989 | Braginetz et al. | 604/195 |
| 4,919,652 | 4/1990 | Alter et al. | 604/110 |

Primary Examiner—John D. Yasko
Assistant Examiner—Mark O. Polutta
Attorney, Agent, or Firm—Seymour G. Bekelnitzky

[57] ABSTRACT

A retractable hypodermic needle & syringe article comprising barrel means comprising means to receive and removably restrain a hypodermic needle-containing assembly for dispensing liquids, plunger means to force the liquids through the needle and a hypodermic needle-containing hub adapted to be removably held at the distal end of the barrel said plunger and hub comprising complementary means to engage, after final use of the article, and retract said hypodermic needle-containing hub into the barrel from which is cannot be reextended for further use wherein the plunger further comprises means to cause the needle-containing hub to assume an angled position relative to the longitudinal axis of the plunger when the hub has been retracted into the barrel.

10 Claims, 5 Drawing Sheets

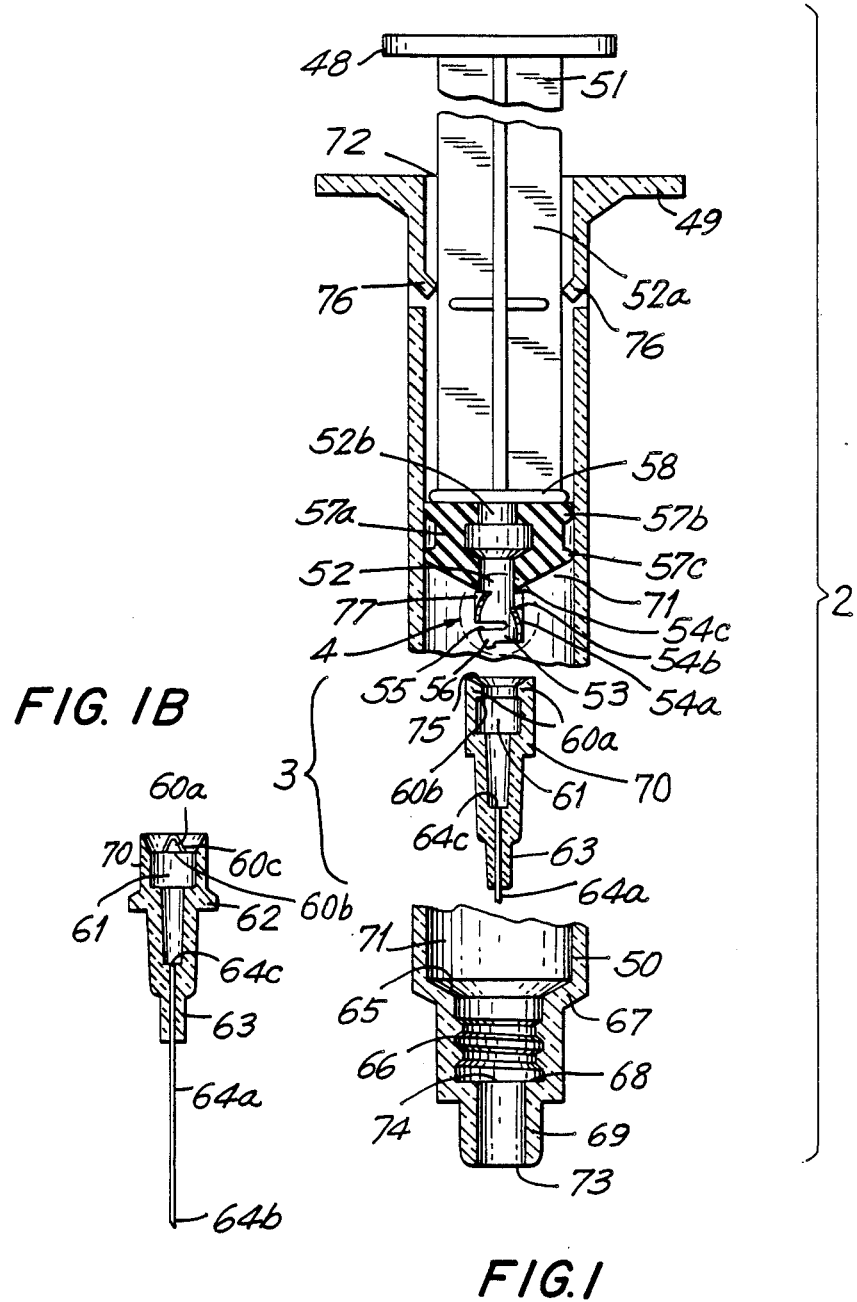
FIG. IB
FIG. I

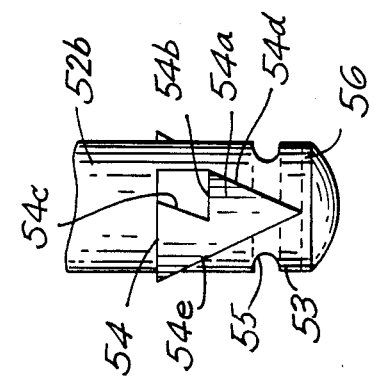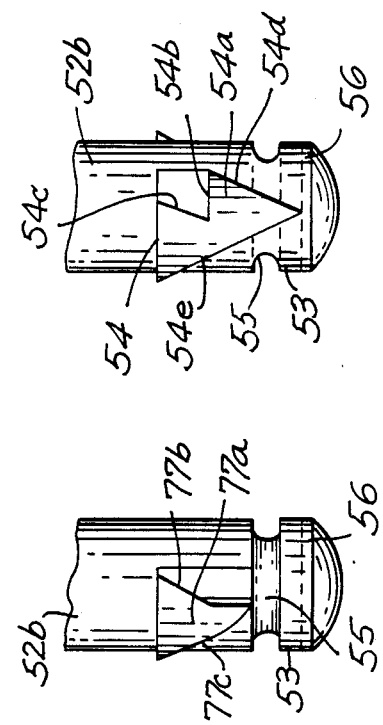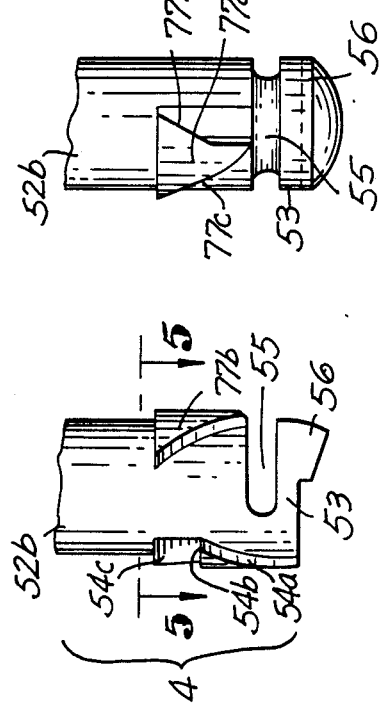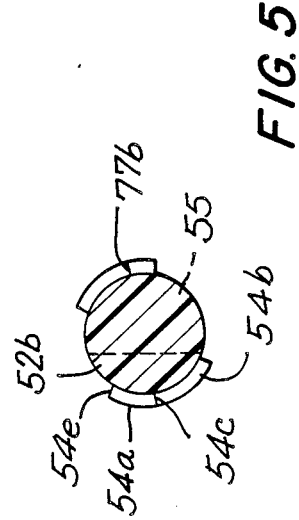

DISPOSABLE HYPODERMIC SYRINGE

This is a continuation-in-part of my copending U.S. patent application serial number 150,621 filed Feb. 8, 1988.

BACKGROUND OF THE INVENTION

This invention relates to hypodermic syringe and needle combinations. More particularly, it relates to a hypodermic syringe and needle combination wherein said needle can be permanently retracted into the syringe barrel, after use, to prevent accidents and abuse of the syringe by causing the needle to be angled relative to the longitudinal axis of the plunger.

Health care workers, such as nurses, and even housekeeping personnel are becoming more fearful of exposure to infectious diseases, such as hepatitis and, especially, AIDS, through transmission thereof by accidental impalation of such personnel on hypodermic needles used, e.g., on patients having such diseases.

It has, therefore, become an imperative to provide syringe and needle combinations which will reduce the possibility of such accidents.

Used needle and syringe combinations have also been implicated in drug abuse situations.

It is therefore, also desirable to provide such combinations which may not easily be reused for such purposes.

Disposable hypodermic needle and syringe combinations, however, must be inexpensive to produce and easy to operate if they are to be widely utilized to avoid such possibilities U.S. Pat. 4,592,744 describes such a combination wherein

[a] standard syringe and needle are mounted in a clear plastic sheath. The needle extends through a hole in the bottom of the sheath. The end of the needle is covered with a cap. To use, the cap is removed and the standard medical procedures are carried out in the usual way but with the syringe still inside of the clear plastic sheath. After use, the syringe and needle are drawn back into the sheath and the needle is completely within the confines of the plastic sheath. Flanges within the sheath catch behind the lip of the needle as the syringe is withdrawn, trapping the needle within the sheath. The needle is thus unable to protrude at either end. (Column 2 lines 16 to 28)

The above system suffers from the fact that it requires a separate sheath to contain the used needle. The cost of the combination, which can be reused is, therefore, increased by the requirement for the separate sheath.

Furthermore, if an abuser were to wish to reuse the needle and syringe it would only be necessary to cut away the sheath and reattach the needle to the syringe.

U.S. Pat. No. 4,702,738 discloses a disposable needle and syringe combination comprising a retractable sheath to cover the needle, after use, and lock in place thereby preventing accidental pricking by the exposed needle or reuse for drug abuse.

This system also suffers from the disadvantages noted above. Thus, if an abuser were to wish to reuse the combination for drug abuse it would only be necessary to cut through the sheath thereby exposing the needle for reuse.

U.S. Pat. No. 4,747,829 discloses a "prefilled syringe ..." which suffers from the fact that it can only be used in "prefilled" condition thus limiting its value. One would be required to have a large number of syringes if one would have many compositions to dispense. Furthermore, one could not use this syringe to withdraw fluids from a source such as a patient.

In addition, the preferred embodiment depends upon a prestressed needle which bows out of alignment with the plunger upon withdrawal from the barrel stem. This, of course, creates difficulties in positioning the needle within the syringe.

In U.S. Pat. No. 4,747,830 there is disclosed a retractable syringe wherein the needle is prevented from redescending through the barrel stem, after withdrawal therefrom, by cooperating latching means in the upper portions of the barrel inner wall and the outer wall of the plunger which lock the needle assembly in an elevated position The latching means are complex and would require expensive tooling.

The patent also discloses means, (see e.g., FIG. 15), in the plunger head to engage the needle assembly for removal from the barrel stem. The engagement means 134 would have to break through a wall of a resilient flexible piston 136, which would require considerable force, before it could engage the needle assembly.

Furthermore, at the time it would be necessary to break through the wall said wall would be entrapped between the engaging means of the plunger and needle assembly thereby increasing the difficulty of breaking through it.

It has now been found that the above disadvantages may be avoided by use of the needle and syringe combination of the instant invention.

SUMMARY OF THE INVENTION

It is an object of the invention to provide a disposable hypodermic needle and syringe combination which reduces the possibility of infecting persons within its proximity by accidental pricking after use on patients suffering from said diseases.

It is another object of the invention to provide a hypodermic needle and syringe combination which cannot, readily, be reused for drug abuse after its required use It is yet another object of the invention to provide a hypodermic needle and syringe combination, as described above, comprising a needle which can be retracted into the barrel of said syringe According to another object of the invention there is provided a needle and syringe combination, as described above, comprising a syringe assembly comprising a barrel comprising a hollow wall having at its proximal end a large opening to receive a plunger adapted to grip and retract a hypodermic needle and, at its distal end a relatively small opening from which descends a hollow stem adapted to removably receive a needle assembly comprising a hollow tube having a sharp distal end and a hub, adherently surrounding said needle, adapted to be gripped and turned by said plunger and withdrawn from said stem by upward movement of said plunger.

It is yet another object of the invention to provide a needle and syringe combination, as described above, wherein the axes of the gripping means on the plunger are skewed relative to the longitudinal axis of the plunger but straighten out upon engagement of said means with the complementary means on the needle assembly when said assembly is within the barrel stem but becomes reskewed upon retraction of the assembly from said stem whereby the needle assembly is caused to take an angular position relative to the barrel stem after withdrawal therefrom.

Another object of the invention is to provide a needle and syringe combination, as described above, further comprising stopping means to prevent complete withdrawal of the plunger from the barrel after the needle assembly has been withdrawn from the barrel stem.

Yet another object of the invention is to provide a needle and syringe combination, as described above, wherein said stopping means comprises projections extending into the barrel cavity from the barrel inner wall to engage with cooperating means on the plunger to prevent further outward movement of the plunger.

Yet another object of the invention is to provide a needle and syringe combination, as described above, further comprising sealing means to prevent liquids contained in said barrel from passing between said barrel inner wall and the plunger outer wall.

Another object of the invention is to provide a hypodermic needle and syringe combination, as described above, which is inexpensive to produce, as it requires no more components than those of the prior art, while providing the extra measure of safety.

According to another object of the invention there is provided a needle and syringe combination, as described above, which is easy to operate and requires no additional actions, to perform the functions of a syringe, on the part of the user, in that it has no more components, compared to the currently available combinations which do not have its safety features Other objects will be in part apparent and in part specifically disclosed in connection with the following detailed description and accompanying drawings wherein like numerals indicate like parts.

DESCRIPTION OF THE DRAWINGS

FIG. 1 is an exploded elevational sectional side view of another embodiment of the invention.

FIG. 1b is a 90° rotational sectional view of the portion of FIG. 1 indicated by the numeral 3.

FIG. 2 is an elevational side view of the portion of the above embodiment indicated by A in FIG. 1.

FIG. 3 is a 90° rotational view of the portion of FIG. 2.

FIG. 4 is a 180° rotational view of the portion of FIG. 2.

FIG. 5 is a sectional elevational view of the portion of FIG. 2 along line 5—5 thereof.

DETAILED DESCRIPTION OF THE PREFERRED EMBODIMENT

Figure 6:
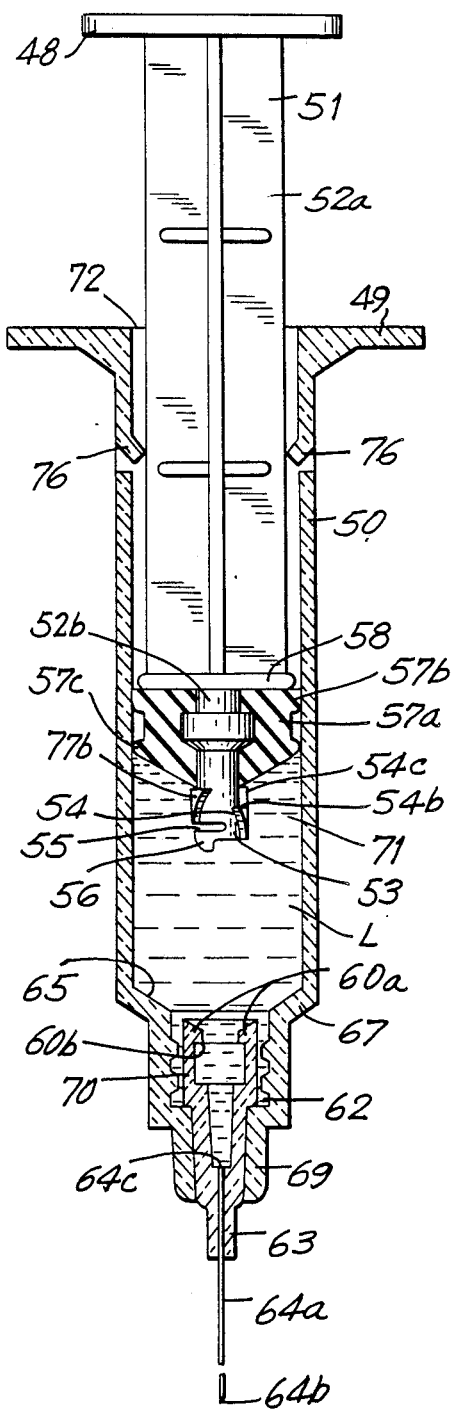
FIG. 6 is an elevational sectional side view of the embodiment of FIG. 1 before expulsion of fluid therefrom.
Figure 7:
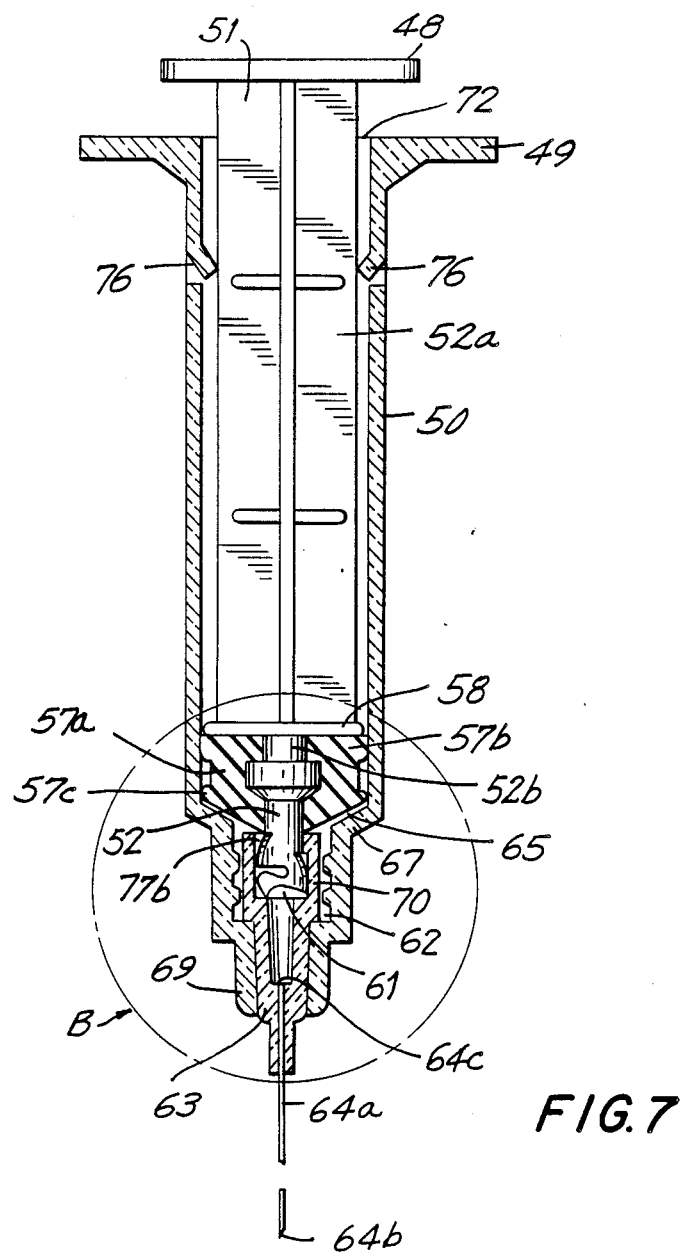
FIG. 7 is an elevational sectional side view of the embodiment of FIG. 1 after expulsion of fluid therefrom.
Figure 8:
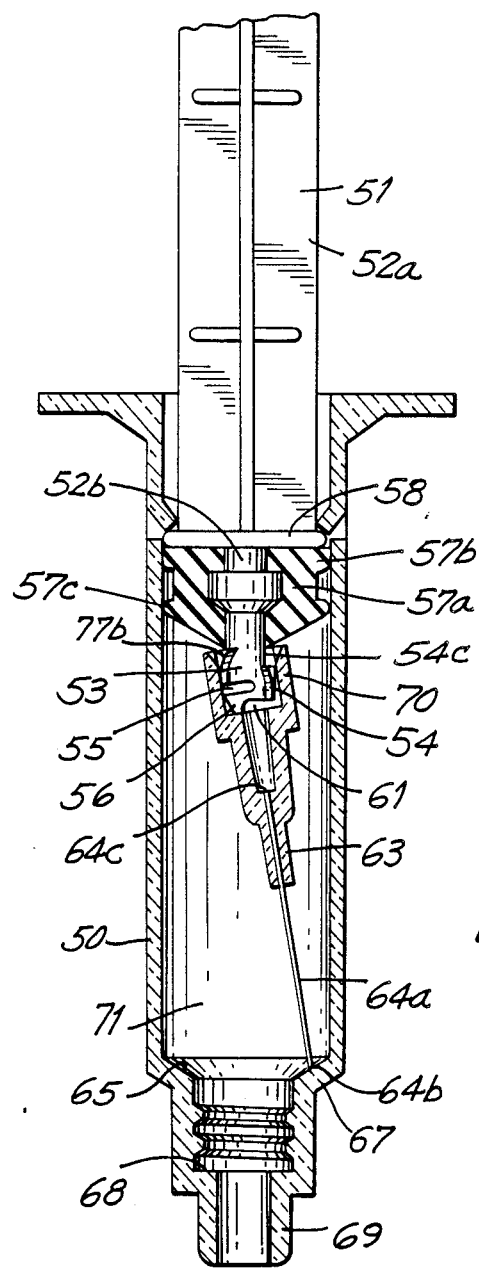
FIG. 8 is an elevational sectional side view of the embodiment of FIG. 1 prior to disposal thereof.

A most preferred embodiment of the invention, as illustrated in FIGS. 1 and 6—8, is generally indicated by the numeral 2. The syringe comprises a barrel comprising an elongated cavity 71 surrounded by a longitudinally extended wall 50 having a large opening 72 at its proximal end, to receive a needle assembly, and a plunger, and a bottom wall 68 at its distal end comprising a small opening 74 from which there descends vertically a hollow stem 69. The longitudinal wall 50 further comprises an annular protrusion 67 extending horizontally inward from the inner surface of wall 50 and spaced from the lower wall 68 of the barrel. The lower wall 68 and protrusion 67 define an annular groove 66 to removably receive cooperatively acting means on a needle assembly to removably lock the needle assembly into place in the barrel stem 69 prior to use of the syringe. The barrel further comprises a flange 49 extending horizontally outward from the upper end of wall 50 to permit gripping of the syringe by the user.

In the aspect of the invention illustrated herein the wall of the groove 66 comprises a threaded portion to cooperatively receive outwardly-directed projections 62 in the outer wall of the stem of the needle assembly.

The inner surface of the upper portion of barrel wall 50 further comprises stopping projections 76 to prevent complete withdrawal of the plunger from the barrel by engaging cooperating means on the plunger.

The hypodermic needle assembly, indicated by the numeral 3, comprises a cavity 61 surrounded by a circular longitudinal elongated wall 70, a large opening 75 at its upper end to receive the distal end of a plunger and a bottom wall comprising a hub 63 adherently surrounding a hollow tube 64a having a sharp distal end 64b, and a proximal opening 64c spaced horizontally inward from wall 70.

The needle assembly 3 further comprises two projections 62 on opposite sides of, and extending normally outward outer surface of the upper portion of hub 63, to be received in the threaded portion 66 of the barrel when the needle assembly is locked into the stem 69.

Wall 70 comprises, on its inner surface, triangular shaped projections 60a, each having a lower horizontal wall 60b and angular side walls 60c rising from the ends thereof to engage cooperating means on a plunger when locking of the needle assembly 3 into, or withdrawal of the assembly from, the stem 69 of the barrel is desired.

The plunger 51 comprises a longitudinally elongated member 52a having a gripping means 48 at its upper end to permit manipulation, such as turning, of the plunger. At its other end the plunger comprises a plunger head 52b extending from, and of smaller diameter than, member 52a. Member 52a and plunger head 52b are separated from each other by a circular horizontal disc 58 whose outer diameter (OD) is slightly less than the inner diameter (ID) of the barrel cavity 71.

The distal end of the plunger comprises a plunger head 52b, indicated by A in FIG. 1 and best discussed in conjunction with FIGS. 2-5, which comprises a notch 55 extending horizontally partially into the plunger head and a flexible portion 53 terminated by a thin arcuate projection 56, on the same side of the plunger head 52b as notch 55.

Notch 55 and tip portion 53 together form a spring which normally, i.e., when the notch is open, causes the flexible tip to be at an angle relative to the longitudinal axis of the plunger, i.e., when the tip and needle assembly are not engaged or when they are engaged in retraction mode and the needle assembly is not in the barrel stem.

The plunger head 52b further comprises a triangular shaped projection 54a having a horizontal upper wall 54 and first and second angular side walls 54d and 54e descending from the ends thereof said projection being situated on the side of the plunger head opposite the notch 55.

An upper portion of projection 54a is cut away inward from side wall 54d to form a notch comprising an angular side wall 54c, approximately parallel to side wall 54d, and a horizontal wall 54b, said notch being adapted to lockingly receive a part of the lower portion of projection 60a of the needle assembly 3.

It has been found that the projection 54a is sometimes sheared off of plunger head 52b by the force applied thereto when the plunger is being twisted while in locking engagement with the needle assembly when said assembly is being withdrawn from the barrel stem 69.

Accordingly this embodiment further comprises a non-locking triangular projection 77a on the side of plunger head 52b opposite locking projection 54a and above notch 55. This projection distributes the force applied by the plunger head to the needle assembly thereby preventing shearing off of locking projection 54a.

The plunger head 52b, at its proximal end, is surrounded by a semi-flexible tube 57a terminated at its upper 57b and lower 57c ends by horizontal flanges whose ODs are equal to or slightly greater than the ID of the barrel. The upper flange 57b abuts the lower surface of disc 58.

Flanges 57b and 57c provide liquid tight sealing of the cavity 71 from the outside while flange 57c acts as a piston to expel fluid from, or draw fluid into, barrel cavity 71.

In the practice of using this embodiment of the invention the syringe and needle assembly is used as any prior art assembly. It is only with respect to safe disposal that this assembly advantageously differs from the prior art articles.

Thus, the syringe may be obtained prefilled with material to be dispensed or it may be filled by withdrawal of liquids from bodies or containers and the liquids then expelled for disposal or injection.

It is sometimes possible that the plunger, after expulsion of the syringe contents, but prior to retraction of the needle assembly, may not completely fill the space between the walls 37 of the hub. The article of the invention may also, as is commonly done, be used to dispense less than all of the contents of the syringe.

Under those circumstances the barrel may, by known methods, be precalibrated.

After all use of the syringe has been completed and safe disposal thereof required the plunger is fully depressed until its tip 53 enters the cavity 61 of the needle assembly. The notch 55, of the plunger, closes and the tip is caused to align with the longitudinal axis of the plunger thereby causing the spring formed by the notch 55 and tip 53 to be under tension.

The plunger is then turned counter clockwise whereby a part of the lower portion of projection 60a of the needle assembly enters the notch in plunger projection 54a causing a portion of the side 60c and bottom 60b walls of the needle assembly projection to make removably locking contact with side 54c and bottom 54b walls of the plunger projection notch.

Counterclockwise turning of the plunger is continued causing the needle assembly projections 62 to disengage from the threaded groove 66 of barrel stem 69.

The plunger is then withdrawn until further withdrawal thereof is prevented by engagement of barrel wall stopping projections 76 and the upper surface of plunger disc 58.

At that time the tip 64b of needle 64a will have been drawn past projection 67 on the barrel and completely into the barrel cavity 71. The tension in the spring formed by plunger notch 55 and tip 53 is relieved, notch 55 opens and the tip 53 is thrown out of alignment with the plunger longitudinal axis whereby the needle assembly 3 will assume the same angle, relative to said axis, as the tip 53.

Any attempt to cause the needle 64a to be reextended will be frustrated by engagement of the needle tip 64b with the upper portion surface 65 of barrel projection 67.

It is to be understood that the directions of turning of the plunger to achieve the desired results may be reversed upon changing the position of the notch in the plunger projection 54a and side 54c and bottom 54b walls thereof.

Furthermore, other means, as known in the art, may be used to prevent complete withdrawal of the plunger from the barrel.

The articles of the invention may be constructed of any materials known to the art which are compatible with the proposed contents and use of the apparatus.

Preferably the barrel will be constructed of transparent materials, to permit viewing the contents thereof, including glass and plastics such as polyethylene, polypylene poly(methylpentene), and the like. If desired, the barrel and plunger may be constructed of different materials. For instance, the barrel may be constructed of poly(methylpentene) and the plunger of polypropylene.

The invention has been described, in detail, with respect to specific embodiments. Modifications and variations maybe made therein within the scope of the invention as defined by the following claims.

What is claimed is:

1. An article comprising a disposable retractable hypodermic needle & syringe apparatus comprising a hypodermic needle-containing assembly and a syringe assembly to receive said hypodermic needle-containing assembly in an extended mode, prior to use, and in a retracted mode, after use, wherein
   (a) said syringe assembly comprises a barrel comprising an elongated cavity, to receive or deliver fluids during use and to receive said needle-containing assembly in its retracted mode, after use thereof, said cavity being surrounded by a wall comprising at its proximal end a large opening, through which a plunger may be passed into said cavity, and at its distal end small opening from which there outwardly extends, coaxially with said cavity, a hollow stem to receive said needle-containing assembly said stem further comprising means to removably interlock with said needle-containing assembly;
   (b) a hypodermic needle-containing assembly comprising a hollow needle, comprising a sharp distal end and a proximal end surrounded by a hub comprising, at its outer wall, second means to removably interlock said hub with the interlocking means of said stem prior to and during use and at the inner wall of its proximal end comprising third means to removably interlock said hub with interlocking means of a plunger, to remove said assembly from its interlock with the stem and retract the assembly from said stem into said cavity to prevent reextension of the needle through said stem; and p1 (c) plunger means comprising an elongated member comprising at its proximal and means for being gripped and turned and, at its distal end, a plunger head comprising:

(1) at its distal end a flexible tip comprising:
  (i) a notch passing partially through said tip, said notch being approximately normal to the longitudinal axis of the tip and spaced proximally from the distal end thereof;
  (ii) a first, triangular, distally-directed projection on the wall thereof opposite said notch and displaced proximally from said notch which may lockingly engage a cooperating projection on the inner wall of the cavity of the needle-containing assembly wherein the upper portion of said first projection is partially removed to provide a horizontal surface, or shelf, extending partially through side projection, and a side wall rising from said shelf to the upper horizontal surface of the projection; and
  (iii) a second projection extending distally from the lower wall of said flexible tip having a curved outer surface; wherein said notch is normally open causing the flexible tip of the plungerhead to be angled relative to the plunger axis and when the tip of the plunger head is in the cavity of the needle assembly the notch is compressed, the tip becomes coaxial with the plunger and the combination of notch and tip form a spring under tension; and
(2) sealing means extending normally outward from the plunger rod and displaced proximally from said flexible tip said means having an outer diameter from about equal to slightly greater than the inner diameter of the barrel to prevent leakage of fluid from the barrel cavity;
(3) piston means extending normally outward from the plunger rod and spaced between the sealing means and the flexible tip said piston means having an outer diameter from about equal to slightly greater than the inner diameter of the barrel to draw fluids into or expel fluids from the barrel cavity; and
(4) stopping means extending normally outward from the plunger rod and spaced proximally from the sealing means, to engage complementary stopping means on the inside of the barrel wall to prevent removal of the plunger and needle-containing assembly from the syringe barrel after retraction of the needle-containing assembly from the barrel stem; wherein the third means on the inside wall of the needle-containing assembly cavity comprise two triangular proximally directed projections on opposite sides of the cavity wall the lower, flat wall of which projection can engage the flat wall of the cutaway portion of the first, triangular projection on the plunger head and the angular wall of the needle-containing assembly can engage the angular wall of said cutaway portion when removal of the needle-containing assembly from the stem and retraction into the barrel cavity is desired.

2. The article of claim 1 further comprising a third, triangular projection on the wall of the plunger tip opposite to the side on which the first projection is situated and spaced proximally from the notch in said tip, whose angular side wall can non-lockingly engage an angular side wall of a triangular projection in the cavity of the hub of the needle-containing assembly to facilitate turning and locking of the needle-containing assembly in the syringe assembly stem.

3. The article according to claim 1 wherein said sealing and piston means comprise a single unit.

4. The article according to claim 1 wherein said sealing and piston means comprise separate units.

5. The article of claim 1 wherein the complementary stopping means comprise inwardly-directed projections at the proximal portion of the inner wall of the barrel.

6. A method of using an article comprising a disposable retractable hypodermic needle & syringe apparatus comprising a hypodermic needle-containing assembly and a syringe assembly to receive said hypodermic needle-containing assembly in an extended mode, prior to use, and in a retracted mode, after use, wherein
  (a) said syringe assembly comprises a barrel comprising an elongated cavity, to receive or deliver fluids during use and to receive said needle-containing assembly in its retracted mode, after use thereof, said cavity being surrounded by a wall comprising at its proximal end a large opening, through which a plunger may be passed into said cavity, and at its distal end a small opening from which there outwardly extends, coaxially with said cavity, a hollow stem to receive said needle-containing assembly said stem further comprising means to removably interlock with said needle-containing assembly;
  (b) a hypodermic needle-containing assembly comprising a hollow needle, comprising a sharp distal end and a proximal end surrounded by a hub comprising, at its outer wall, second means to removably interlock said hub with the interlocking means of said stem prior to and during use and at the inner wall of its proximal end comprising third means to removably interlock said hub with interlocking means of a plunger, to remove said assembly from its interlock with the stem and retract the assembly from said stem into said cavity to prevent reextension of the needle through said stem; and
  (c) plunger means comprising at its proximal end means for being gripped and turned and, at its distal end, a plunger head comprising:
    (1) at its distal end a flexible tip comprising:
      (i) a notch passing partially through said tip, said notch being approximately normal to the longitudinal axis of the tip and spaced proximally from the distal end thereof;
      (ii) a first, triangular, distally-directed projection on the wall thereof opposite said notch and displaced proximally from said notch which may locking engage a cooperating projection on the inner wall of the cavity of the needle-containing assembly wherein the upper portion of said first projection is partially removed to provide a horizontal surface, or shelf, extending partially through said projection, and a side wall rising from said shelf to the upper horizontal surface, or shelf, extending partially through said projection, and a side all rising from said shelf to the upper horizontal surface of the projection; and
      (iii) a second projection extending distally from the lower wall of said flexible tip having a curved outer surface;
        wherein said notch is normally open causing the flexible tip of the plunger head to be angled relative to the plunger axis and when the tip of the plunger head is in the cavity of the needle assembly the notch is compressed, the tip becomes coaxial with the plunger and the combination of notch and tip form a spring under tension; and (2) sealing means extending normally outward from the plunger rod and displaced proximally from said flexible tip said means having an outer diameter from about equal to slightly greater than the inner diameter of the barrel to prevent leakage of fluid from the barrel cavity;

(3) piston means extending normally outward from the plunger rod and spaced between the sealing means and the flexible tip said piston means having an outer diameter from about equal to slightly greater than the inner of the barrel to draw fluids into or expel fluids from the barrel cavity; and (4) stopping means extending normally outward from the plunger rod and spaced proximally from the sealing means, to engage complementary stopping means on the inside of the barrel wall to prevent removal of the plunger and needle-containing assembly from the syringe barrel after retraction of the needle-containing from the syringe barrel after retraction of the needle-containing assembly from the barrel stem; wherein the third means on the inside wall of the needle-containing assembly cavity comprise two triangular proximally directed projections on opposite sides of the cavity wall the lower, flat wall of which projection can engage the flat wall of the cutaway portion of the first, triangular projection on the plunger head and the angular wall of the needle-containing assembly can engage the angular wall of said cutaway portion when removal of the needle-containing assembly from the stem and retraction into the barrel cavity is desired; which comprises the step of:

(1) filling said barrel with and dispensing the liquids contained therein;

(2) after the last dispension further inserting and rotating the plunger until angular and flat portions of the first, triangular projection on the plunger head lockingly engage the angular and flat portions, respectively, of a triangular projection on the needle-containing assembly and the notch in the flexible tip is closed placing it under tension; and (3) removing the hub from the stem and retracting same until the distal end of the needle passes the lower, small opening, and enters the cavity, of the barrel wherein the notch of the plunger head flexible tip opens canting the tip and the needle-containing assembly attached thereto whereby the needle-containing assembly is retained in the syringe barrel and prevented from being reextended through the barrel stem.

7. The method of claim 6 wherein the plunger head comprises a third, triangular projection on the wall of the plunger tip opposite to the side on which the first projection is situated and spaced proximally from the notch in said tip, whose angular side wall can non-lockingly engage an angular side wall of a triangular projection in the cavity of the hub of the needle-containing assembly to distribute turning forces and facilitate turning and locking of the needle-containing assembly in the syringe assembly stem.

8. The method according to claim 7 wherein said sealing and piston means comprise a single unit.

9. The method according to claim 7 wherein said sealing and piston means comprise separate units.

10. The article of claim 6 wherein said projections are formed after insertion of the plunger into the barrel.

* * * * *

UNITED STATES PATENT AND TRADEMARK OFFICE
CERTIFICATE OF CORRECTION

PATENT NO. : 4,986,813

DATED : Jan. 22, 1991

INVENTOR(S) : Blake, III et al.

It is certified that error appears in the above-identified patent and that said Letters Patent is hereby corrected as shown below:

On the title page, item [73] should read as follows:

-- The Medtech Group, Inc., South Plainfield, NJ --

Signed and Sealed this

Third Day of September, 1991

*Attest:*

HARRY F. MANBECK, JR.

*Attesting Officer*     *Commissioner of Patents and Trademarks*

UNITED STATES PATENT AND TRADEMARK OFFICE
CERTIFICATE OF CORRECTION

PATENT NO.   : 4,986,813
DATED        : Jan. 22, 1991
INVENTOR(S)  : Blake, III et al.

It is certified that error appears in the above-identified patent and that said Letters Patent is hereby corrected as shown below:

On the title page, item [73] should read as follows:
    --The MedTech Group, Inc., South Plainfield, NJ--

This certificate supersedes Certificate of Correction issued September 3, 1991.

Signed and Sealed this

Ninth Day of June, 1992

Attest:

DOUGLAS B. COMER

*Attesting Officer*     Acting Commissioner of Patents and Trademarks